US006422993B1

(12) United States Patent
Hudson

(10) Patent No.: US 6,422,993 B1
(45) Date of Patent: Jul. 23, 2002

(54) SEXUAL AID SYSTEM

(76) Inventor: Donald E. Hudson, 5830 Bahia Honda Way S., St. Petersburg, FL (US) 33706-2228

( * ) Notice: Subject to any disclaimer, the term of this patent is extended or adjusted under 35 U.S.C. 154(b) by 0 days.

(21) Appl. No.: 09/608,255

(22) Filed: Jun. 30, 2000

(51) Int. Cl.[7] .................................................... A61F 5/00
(52) U.S. Cl. ......................................................... 600/38
(58) Field of Search .............................. 600/38, 39, 40, 600/41; 601/46, 49, 51, 53, 54, 67, 69, 70; 128/845

(56) References Cited

U.S. PATENT DOCUMENTS 4,790,296 A * 12/1988 Segal .......................... 600/38
5,676,637 A * 10/1997 Lee ............................. 601/49
5,725,473 A * 3/1998 Taylor .......................... 600/38
6,142,929 A * 11/2000 Padgett ........................ 600/38

OTHER PUBLICATIONS

Lampert, Dave, "Sybian . . . For Women", 2000, http://www.sybian.com, pp. 1–9.*

* cited by examiner

*Primary Examiner*—Kevin Shaver
*Assistant Examiner*—Brian Szmal

(57) ABSTRACT

A sexual aid system has a housing with apertures in the front and devices therein. The devices include an upper vibrator, two lower inserts in the shape of a penis and a larger penis. Separate drivers include a mechanism to effect the rapid orbital movement of the vibrator, a rotary motor and a linkage coupling the motor with each insert to effect the axial reciprocation of the inserts. A controller having switches to turn off and on the rotary motor, power to the vibrator, and dials to vary the speed of the stroke of the lower inserts.

3 Claims, 3 Drawing Sheets

FIG 3
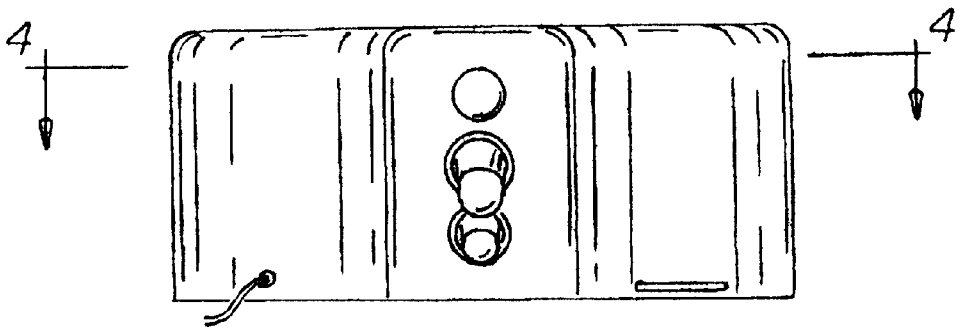
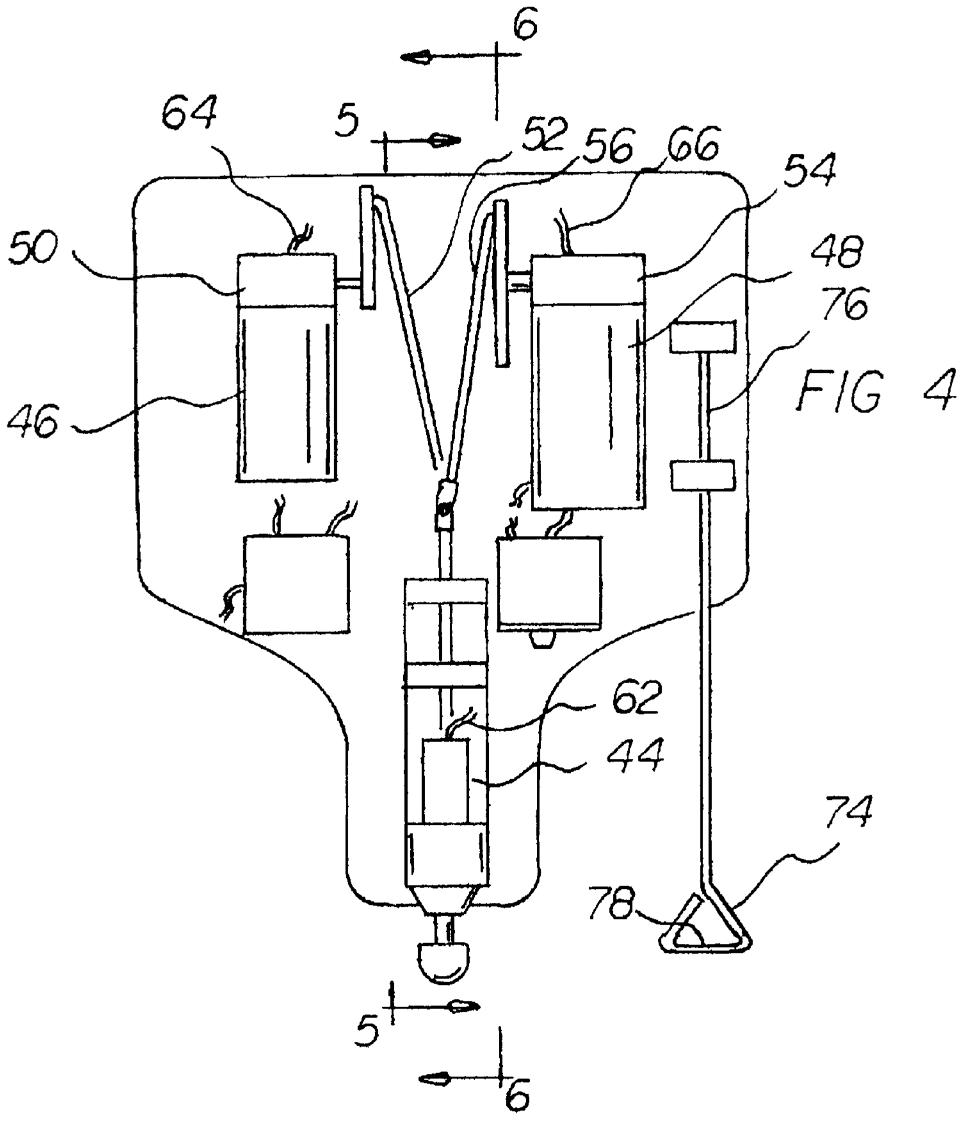
FIG 4

FIG 5
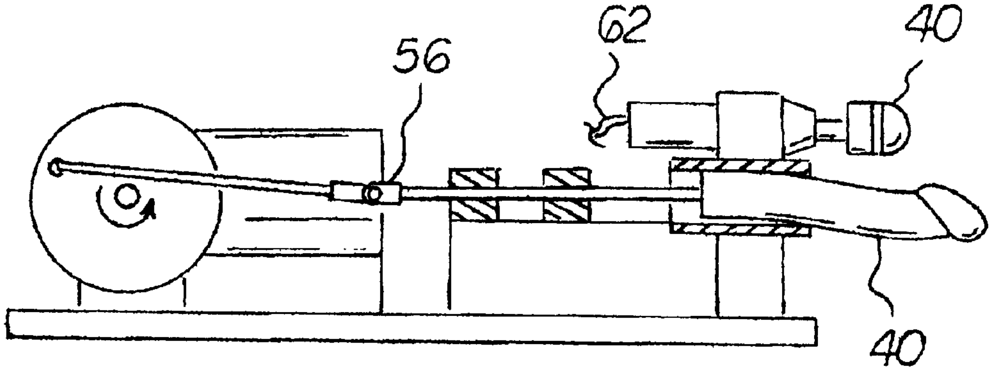
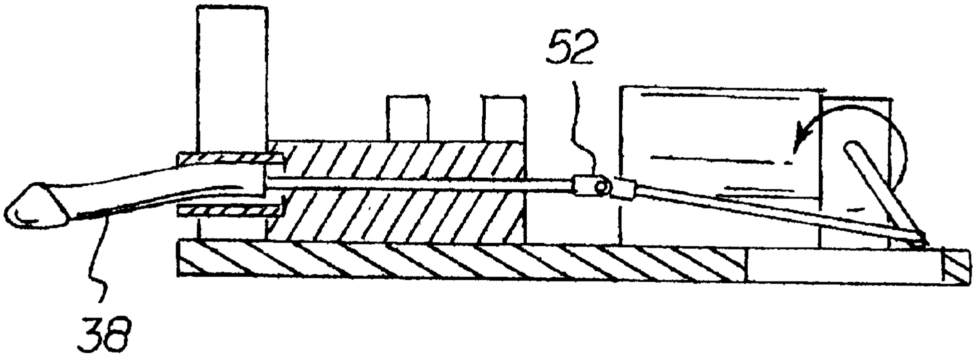
FIG 6

SEXUAL AID SYSTEM

BACKGROUND OF THE INVENTION

1. Field of the Invention

The present invention relates to a sexual aid system and more particularly pertains to providing therapeutic relief and stimulation to a female user.

2. Description of the Prior Art

The use of sexual devices of known designs and configurations is known in the prior art. More specifically, sexual devices of known designs and configurations previously devised and utilized for the purpose of providing therapeutic relief and/or sexual stimulation through known methods and apparatuses are known to consist basically of familiar, expected, and obvious structural configurations, notwithstanding the myriad of designs encompassed by the crowded prior art which has been developed for the fulfillment of countless objectives and requirements.

By way of example, U.S. Pat. No. 4,722,327 TO William J. Harvey discloses a therapeutic apparatus. U.S. Pat. No. 4,790,296 to Segal discloses a sexual stimulation apparatus. U.S. Pat. No. 4,846,158 to Teranishi discloses a hand type electric massage machine. U.S. Pat. No. 5,076,261 to Black discloses a motor-driven therapeutic apparatus. U.S. Pat. No. 5,460,597 to Hopper discloses a portable hand-held vibratory feminine stimulator. Lastly, U.S. Pat. No. 5,725,473 to Taylor discloses a sexual aid.

While these devices fulfill their respective, particular objectives and requirements, the aforementioned patents do not describe sexual aid system that allows providing therapeutic relief and stimulation to a female user.

In this respect, the sexual aid system according to the present invention substantially departs from the conventional concepts and designs of the prior art, and in doing so provides an apparatus primarily developed for the purpose of providing therapeutic relief and stimulation to a female user.

Therefore, it can be appreciated that there exists a continuing need for a new and improved sexual aid system which can be used for providing therapeutic relief and stimulation to a female user. In this regard, the present invention substantially fulfills this need.

SUMMARY OF THE INVENTION

In view of the foregoing disadvantages inherent in the known types of sexual devices of known designs and configurations now present in the prior art, the present invention provides an improved sexual aid system. As such, the general purpose of the present invention, which will be described subsequently in greater detail, is to provide a new and improved sexual aid system and method which has all the advantages of the prior art and none of the disadvantages.

To attain this, the present invention essentially comprises a first provided is a housing. The housing has an upper plate and a lower plate in parallel relationship. The plates have an essentially common peripheral size and shape. A peripheral wall is located between the plates. The plates and wall form a rearward portion in an enlarged generally rectilinear configuration and a forward-portion in a smaller essentially rectilinear configuration. The plates and wall have a forward essentially vertical area. Three vertically aligned apertures are provided through the forward vertical area. The apertures include an upper aperture, a lower aperture and an intermediate aperture. A plurality of devices are positioned within the housing and individually extend through the apertures to exterior of the housing. The devices include an upper vibrator extending through the upper aperture. The devices also include a lower insert in the shape of a smaller penis extending through the lower aperture. The devices also include an upper insert in the shape of a larger penis extending through the intermediate aperture. A plurality of drivers are provided. The drivers are operatively coupled with respect to the devices located within the housing. The drivers include a mechanism to effect the rapid orbital movement of the vibrator axially with respect to the first aperture for contacting the clitoris of a user. The drivers also include a second driver including a primary rotary motor and a two bar linkage coupling the motor with the lower insert to effect the axial reciprocation of the lower insert with respect to the lower aperture for contacting the anus of the user, if desired. The drivers also include a third driver including a secondary rotary motor with a two bar linkage coupling the motion with the upper insert for the axial reciprocation of the upper insert with respect to the intermediate aperture for contacting the vagina of a user. Next provided is a controller. The controller is located exterior of the housing with leads electrically coupled to the first driver and a second driver and a third driver for the individual energization of the drivers. The controller includes a first switch to turn off and on the rotary motors to the upper and lower inserts. The controller also includes a second switch to turn on and off power-to the vibrator. The controller also includes a first dial to vary the speed of the stroke of the lower inserts to a maximum of 120 strokes per minute independent of the speed of the vibrator and the upper insert. The controller also includes a second dial to vary the speed of the upper insert up to 120 cycles per minute independent of the speed of the vibrator and the lower insert. Lastly provided is a handle. The handle has a rearward end coupled to the housing. The handle also has a forward end adapted to be grasped by a user for moving the housing toward or away from the user during operation and use.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved sexual aid system which has all of the advantages of the prior art sexual devices of known designs and configurations and none of the disadvantages.

It is another object of the present invention to provide a new and improved sexual aid system which may be easily and efficiently manufactured and marketed.

It is further object of the present invention to provide a new and improved sexual aid system which is of durable and reliable constructions.

An even further object of the present invention is to provide a new and improved sexual aid system which is susceptible of a low cost of manufacture with regard to both materials. and labor, and which accordingly is then susceptible of low prices of sale to the consuming public, thereby making such sexual aid system economically available to the buying public.

Even still another object of the present invention is to provide a sexual aid system for providing therapeutic relief and stimulation to a female user.

Lastly, it is an object of the present invention to provide a new and improved sexual aid system including a housing with an upper plate and a lower plate with a peripheral wall there between and a forward essentially vertical area with a plurality of vertically aligned apertures there through including an upper aperture and lower aperture. A plurality of devices are positioned within the housing and individually extend through the apertures to exterior of the housing. The devices include an upper vibrator extending through the upper aperture and a lower insert in the shape of a penis extending through the lower aperture. A plurality of drivers are operatively coupled with respect to the devices located within the housing. The drivers include a mechanism to effect the rapid orbital movement of the vibrator with respect to the first aperture. A second driver includes a rotary motor and a linkage coupling the motor with the lower insert to effect the axial reciprocation of the lower insert with respect to the lower aperture. A controller is located exterior of the housing with leads electrically coupled to the first driver and a second driver. The controller includes a first switch to turn off and on the rotary motor to the lower inserts, a second switch to turn on and off power to the vibrator, and a dial to vary the speed of the stroke of the lower inserts.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is a front elevational view taken along line 3—3 of FIG. 2.

FIG. 4 is a cross sectional view taken along line 4—4 of FIG. 3.

FIG. 5 is a cross sectional view taken along line 5—5 of FIG. 4 but illustrating an alternate embodiment of the invention with but a single reciprocating insert.

FIG. 6 is a cross sectional view taken along line 6—6 of FIG. 4 but illustrating an alternate embodiment of the invention using a single reciprocating insert.

The same reference numerals refer to the same parts throughout the various Figures.

DESCRIPTION OF THE PREFERRED EMBODIMENT

Figure 1:
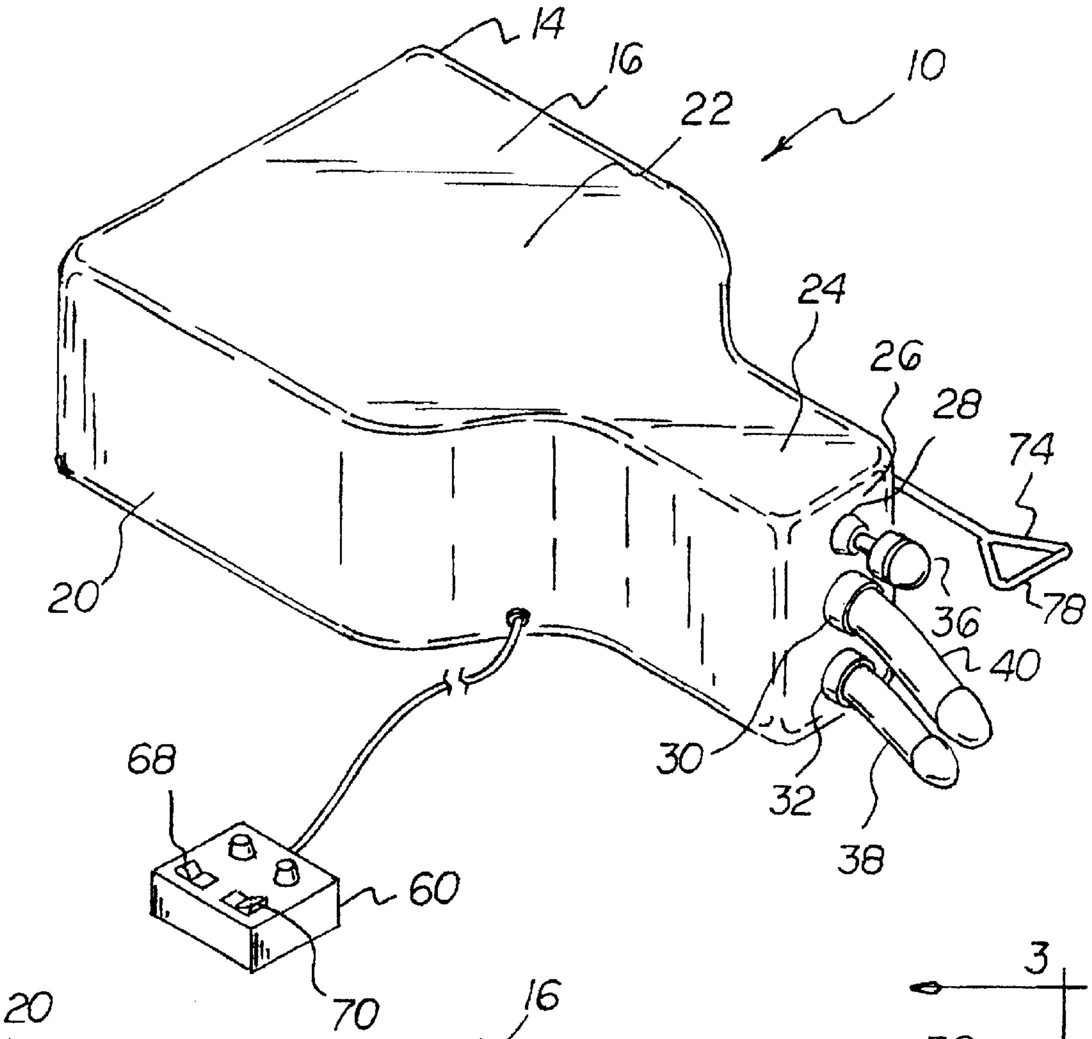
FIG. 1 is a perspective illustration of the new and improved sexual aid system constructed in accordance with the principles of the present invention.
Figure 2:
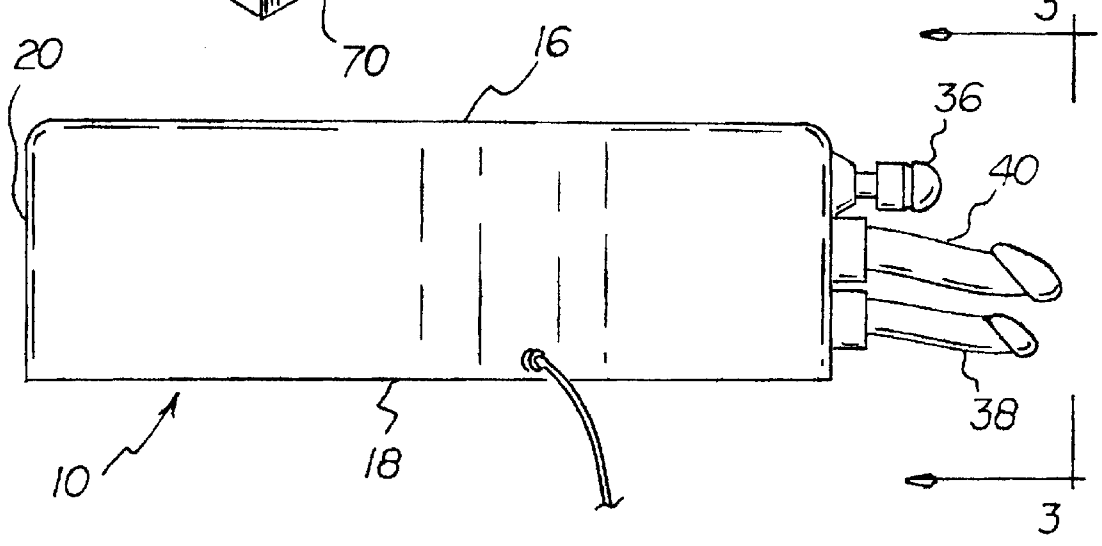
FIG. 2 is a side elevational view of the system shown in FIG. 1.

With reference now to the drawings, and in particular to FIG. 1 thereof, the preferred embodiment of the new and improved sexual aid system embodying the principles and concepts of the present invention and generally designated by the reference numeral 10 will be described.

The present invention, the sexual aid system 10 is comprised of a plurality of components. Such components in their broadest context include a housing, a plurality of devices positioned within the housing, a plurality of drivers, and a controller. Such components are individually configured and correlated with respect to each other so as to attain the desired objective.

First provided is a housing 14. The housing has an upper plate 16 and a lower plate 18 in parallel relationship. The plates have an essentially common peripheral size and shape. A peripheral wall 20 is located between the plates. The plates and wall form a rearward portion 22 in an enlarged generally rectilinear configuration and a forward portion 24 in a smaller essentially rectilinear configuration. The plates and wall have a forward essentially vertical area 26. Three vertically aligned apertures 28, 30, 32 are provided through the forward vertical area. The apertures include an upper aperture 28, a lower aperture 30 and an intermediate aperture 32.

A plurality of devices are positioned within the housing and individually extend through the apertures to exterior of the housing. The devices include an upper vibrator 36 extending through the upper aperture. The devices also include a lower insert 38 in the shape of a smaller penis extending through the lower aperture. The devices also include an upper insert 40 in the shape of a larger penis, extending through the intermediate aperture.

A plurality of drivers 44, 46, 48 are provided. The drivers are operatively coupled with respect to the devices located within the housing. The drivers include a mechanism 44 to effect the rapid orbital movement of the vibrator axially with respect to the first aperture for contacting the clitoris of a user. The drivers also include a second driver 44 including a primary rotary motor 50 and a two bar linkage 52 coupling the motor with the lower insert to effect the axial reciprocation of the lower insert with respect to the lower aperture for contacting the anus of the user, if desired. The drivers also include a third driver including a secondary rotary motor 54 with a two bar linkage 56 coupling the motion with the upper insert for the axial reciprocation of the upper insert with respect to the intermediate aperture for contacting the vagina of a user.

Next provided is a controller 60. The controller is located exterior of the housing with leads 62, 64, 66 electrically coupled to the first driver and a second driver and a third driver for the individual energization of the drivers. The controller includes a first switch 68 to turn off and on the rotary motors to the upper and lower inserts. The controller also includes a second switch 70 to turn on and off power to the vibrator. The controller also includes a first dial to vary the speed of the stroke of the lower inserts to a maximum of 120 strokes per minute independent of the speed of the vibrator and the upper insert. The controller also includes a second dial to vary the speed of the upper insert up to 120 cycles per minute independent of the speed of,the vibrator and the lower insert.

Lastly provided is a handle 74. The handle has a rearward end 76 coupled to the housing. The handle also has a forward end 78 adapted to be grasped by a user for moving the housing toward or away from the user during operation and use.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A sexual aid system for providing therapeutic relief and stimulation to a female user comprising, in combination:

a housing having an upper plate and a lower plate in parallel relationship with an essentially common peripheral size and shape with a peripheral wall there between, the plates and wall forming a rearward portion in an enlarged generally rectilinear configuration and a forward portion in a smaller essentially rectilinear configuration and having a forward essentially vertical area with three vertically aligned apertures there through including an upper aperture, a lower aperture and an intermediate aperture there between;

a plurality of devices positioned within the housing and individually extending through the apertures to exterior of the housing, the devices including an upper vibrator extending through the upper aperture, a lower insert in the shape of a smaller penis extending through the lower aperture and an upper insert in the shape of a larger penis extending through the intermediate aperture;

a plurality of separate drivers operatively coupled with respect to the devices located within the housing, the drivers including a mechanism to effect the rapid orbital movement of the vibrator axially with respect to the first aperture for contacting the clitoris of a user, a second driver including a primary rotary motor and a two bar linkage coupling the motor with the lower insert to effect the axial reciprocation of the lower insert, with respect to the lower aperture for contacting the anus of the user, if desired, and the third driver including a secondary rotary motor with a two bar linkage coupling the motion with the upper insert for the axial reciprocation of the upper insert with respect to the intermediate aperture for contacting the vagina of a user; and a controller located exterior of the housing with first leads electrically coupled to the first driver and second leads electrically coupled to a second driver and third leads electrically coupled to a third driver for the individual energization thereof, the controller including a first switch to turn off and on the rotary motors to the upper and lower inserts, a second switch to turn on and off power to the vibrator, a first dial to vary the speed of the stroke of the lower inserts to a maximum of 120 strokes per minute independent of the speed of the vibrator and the upper insert and a second dial to vary the speed of the upper insert up to 120 cycles per minute independent of the speed of the vibrator and the lower insert; and a handle having a rearward end coupled to the housing and a forward end adapted to be grasped by a user for moving the housing toward or away from the user during operation and use.

2. A sexual aid system comprising:

a housing having an upper plate and a lower plate with a peripheral wall there between and having a forward essentially vertical area with a plurality of vertically aligned apertures there through including an upper aperture and lower aperture;

a plurality of devices positioned within the housing and individually extending through the apertures to exterior of the housing, the devices including an upper vibrator extending through the upper aperture and a lower insert in the shape of a smaller penis extending through the lower aperture;

a third aperture in the housing between the first and second apertures with a third device in the form of a larger penis reciprocable with respect thereto:

a plurality of separate drivers operatively coupled individually with respect to the three devices located within the housing, the drivers including a mechanism to effect the rapid orbital movement of the vibrator with respect to the first aperture and a second driver including a rotary motor and a linkage coupling the motor with the smaller penis to effect the axial reciprocation of the smaller penis with respect to the lower aperture and a third driver including a rotary motor and a linkage coupling the motor with the larger penis to effect the axial reciprocation of the larger penis with respect to the third aperture; and a controller located exterior of the housing with separate leads electrically coupled to the first driver and a second driver and third driver, the controller including a first switch to turn off and on the rotary motor to the lower inserts, a second switch to turn on and off power to the vibrator, and dials to individually vary the speed of the strokes of the smaller penis and larger penis.

3. The system as set forth in claim 2 and further including a handle having a rearward end coupled to the housing and a forward end adapted to be grasped by a user for moving the housing toward or away from the user during operation and use.

* * * * *